United States Patent

Matsumoto et al.

[11] Patent Number: 6,100,292
[45] Date of Patent: Aug. 8, 2000

[54] KETONE DERIVATIVES AND THEIR MEDICAL APPLICATIONS

[75] Inventors: Tsuyoshi Matsumoto; Hideki Kawai, both of Kamakura; Kiyoshi Okano, Koza-gun; Katsuyuki Mori, Kamakura; Yasumoto Adachi, Yokohama, all of Japan

[73] Assignee: Toray Industries, Inc., Tokyo, Japan

[21] Appl. No.: 09/317,927

[22] Filed: May 25, 1999

[30] Foreign Application Priority Data

Sep. 26, 1997 [JP] Japan ................................. 9-262032

[51] Int. Cl.⁷ .......................... A61K 31/38; A61K 31/35; C07D 409/00; C07D 333/64; C07D 311/04
[52] U.S. Cl. .......................... 514/443; 514/457; 514/460; 514/432; 514/444; 549/59; 549/54; 549/55; 549/28; 549/23; 549/289; 549/287; 549/291; 549/305; 549/313; 549/318
[58] Field of Search ..................... 549/289, 287, 549/291, 305, 313, 318, 59, 54, 55, 28, 23; 514/457, 460, 443, 444, 432

[56] References Cited

U.S. PATENT DOCUMENTS

| | | |
|---|---|---|
| 3,963,756 | 6/1976 | Ohno et al. . |
| 4,061,769 | 12/1977 | Ohno et al. . |
| 5,059,620 | 10/1991 | Stout et al. . |
| 5,073,563 | 12/1991 | Frickel et al. ............... 514/365 |
| 5,424,320 | 6/1995 | Fortin et al. ................ 514/337 |
| 5,905,088 | 5/1999 | Diaz et al. .................. 514/468 |

FOREIGN PATENT DOCUMENTS

| | | |
|---|---|---|
| 0 071 535 | 7/1982 | European Pat. Off. . |
| 0 841 063 A1 | 5/1998 | European Pat. Off. . |
| 63-239224 | 10/1988 | Japan . |
| 97/35565 | 10/1997 | WIPO . |

OTHER PUBLICATIONS

J. Med. Chem. 1993, 36, 3386–3396 Rowley et al 3–Acyl–4–hydroxyquinolin–2(1H)–ones.

*Primary Examiner*—Deborah C. Lambkin
*Attorney, Agent, or Firm*—Nixon & Vanderhye

[57] ABSTRACT

This invention relates to ketones represented by the following formula

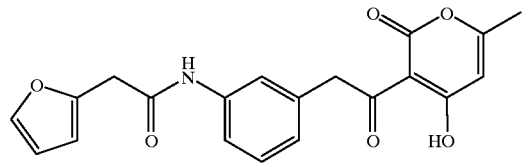

and to drugs in which such a ketone or pharmacologically acceptable salt thereof is an effective component.

The ketones of the present invention encourage the production of platelets, red blood cells, white blood cells and the like, and can be used to prevent or treat cytopaenia brought about by cancer chemotherapy, radiotherapy, bone marrow transplantation and drug therapy, or by immunological abnormality or anaemia, and the like.

9 Claims, 1 Drawing Sheet

Fig. 1

KETONE DERIVATIVES AND THEIR MEDICAL APPLICATIONS

TECHNICAL FIELD

The present invention relates to ketone derivatives, and to drugs in which the ketone derivatives or pharmacologically acceptable salts thereof are an effective component, in particular haemopoietic agents.

TECHNICAL BACKGROUND

As compounds analogous to the ketone derivatives relating to the present invention, there are reported examples of 3-(1-phenyl-2-acetyl)-4-hydroxypyrone analogues and 3-(1-phenyl-2-acetyl)-4-hydroxycoumarin analogues, but they differ from the ketone derivatives relating to the present invention in that they do not have an amide linkage.

With regard to the applications of lactones, the compounds described for example in Japanese Unexamined Patent Publication (Kokai) No. 5-43568 and EP 0508690 are known as anti-inflammatory agents with phospholipase $A_2$ inhibitory activity; the compounds described in *Archive des Pharmazie* (Weinhelm, Ger.) (1983), 316(2), 115–120 are known as anti-coagulating agents; and the compounds described in J. Anitbiot., 47(2), 143–7 (1994) are known as an anti-Aids drug with HIV-protease inhibitory activity. With regard to the applications of lactams, the compounds described in for example *Chem. Pharm. Bull*, 32(10), 4197–4204 (1984) are known as drugs with antimicrobial activity and the compounds described in Antibiot., 33(2), 173–181 (1980) are known as anaerobic antibiotics.

However, ketone derivatives with a haemopoietic action are totally unknown. The present invention has the objective of offering ketone derivatives with an outstanding haemopoietic action.

DISCLOSURE OF THE INVENTION

The aforesaid objective is realized by means of the present invention as described below.

Specifically, the present invention relates to ketone derivatives represented by the following general formula (I)

(where A denotes general formula (II) or (III)

m is the integer 1 or 2, $R_1$ to $R_{11}$ are each independently a hydrogen atom or substituent group, and n is 0 or 1), in particular to the ketone derivatives or the pharmacologically acceptable salts of the ketone derivatives where $R_1$ to $R_7$ are each independently a hydrogen atom or a substituent selected from the group comprising the fluorine atom, chlorine atom, bromine atom, $C_2$ to $C_{19}$ alkyl groups, $C_2$ to $C_{19}$ alkenyl groups, $C_6$ to $C_{12}$ aryl groups, $C_6$ to $C_{12}$ aryl groups with a $C_1$ to $C_{19}$ alkyl, $C_1$ to $C_{19}$ alkyl groups with a $C_6$ to $C_{12}$ aryl group, $C_6$ to $C_{12}$ aryl groups with a $C_2$ to $C_{19}$ alkenyl, $C_2$ to $C_{19}$ alkenyl groups with a $C_6$ to $C_{12}$ aryl group, the hydroxyl group, $C_1$ to $C_{10}$ alkoxy groups, the nitro group, carboxyl group, $C_2$ to $C_{10}$ alkoxycarbonyl groups, and the cyano group, or $R_1$ and $R_2$ are together —CH=CH—CH=CH—, $R_5$ and $R_6$ are together —CH=CH—CH=CH— or —(CH$_2$)$_q$— (q is an integer in the range 2 to 5), or $R_6$ and $R_7$ are together —(CH$_2$)$_r$— (r is an integer in the range 2 to 5),

$R_8$ and $R_9$ are each independently a hydrogen atom, or a substituent selected from the group comprising $C_2$ to $C_6$ alkyl groups, $C_2$ to $C_6$ alkenyl groups, $C_6$ to $C_{12}$ aryl groups, $C_6$ to $C_{12}$ aryl groups with a $C_1$ to $C_{19}$ alkyl, $C_1$ to $C_{19}$ alkyl groups with a $C_6$ to $C_{12}$ aryl group, $C_6$ to $C_{12}$ aryl groups with a $C_2$ to $C_{19}$ alkenyl group, $C_2$ to $C_{19}$ alkenyl groups with a $C_6$ to $C_{12}$ aryl group, and $C_2$ to $C_{10}$ alkoxycarbonyl groups, or $R_8$ and $R_9$ are together —(CH$_2$)$_4$— or —(CH$_2$)$_5$—, $R_{10}$ is a fluorine atom, chlorine atom or bromine atom, $R_{11}$ is a $C_1$ to $C_6$ alkyl group or $C_6$ to $C_{12}$ aryl group, or $R_{10}$ and $R_{11}$ are together —CH=CH—CH=CH— or —(CH$_2$)$_t$— (t is an integer in the range 2 to 5); and to drugs containing the ketone derivatives represented by general formula (I) or pharmacologically acceptable salts thereof, in particular haemopoietic agents.

Optimum Mode for Practising the Invention

When Z in general formula (I) of the present invention is a hydrogen atom, the ketoenol tautomers of the following formulae are included.

-continued

Here, the $C_2$ to $C_{19}$ alkyl groups in general formula (I) may be straight-chain, branched or cyclic, and examples are methyl, ethyl, n-propyl, isopropyl, n-butyl, isobutyl, sec-butyl, tert-butyl, n-pentyl, isopentyl, neopentyl, tert-pentyl, n-hexyl, n-heptyl, n-octyl, n-nonyl, n-decyl, n-dodecyl, n-tetradecyl, n-pentadecyl, n-hexadecyl, n-heptadecyl, 15-methylhexadecyl, 7-methylhexadecyl, n-octadecyl, n-nonadecyl, eicosyl, tetracosyl, 24-methyltetracosyl, cyclopropyl, cyclobutyl, cyclohexyl and the like. The $C_1$ to $C_{19}$ alkenyl groups may be straight-chain or branched, and include isomers pertaining to the double bond (E or Z isomers). Examples are ethenyl, 2-propenyl, 2-butenyl, 2-pentenyl, 2-hexenyl, 2-heptenyl, 2-octenyl, 2-nonenyl, 2-decenyl, 3-butenyl, 3-pentenyl, 3-hexenyl, 3-heptenyl, 3-octenyl, 3-nonenyl, 3-decenyl, 4-pentenyl, 4-hexenyl, 4-heptenyl, 4-octenyl, 4-nonenyl, 4-decenyl, 1,3-butadienyl, 1,3-pentadienyl, 1,3-hexadienyl, 1,3-heptadienyl, 1,3-octadienyl, 1,3-nonadienyl, 1,3-decadienyl, 1,4-pentadienyl, 1,4-hexadienyl, 1,4-heptadienyl, 1,4-octadienyl, 1,4-nonadienyl, 1,4-decadienyl, 1,3,5-hexatrienyl, 1,3,5-heptatrienyl, 1,3,5-octatrienyl, 1,3,5-nonatrienyl, 1,3,5-decatrienyl and the like.

The aryl groups may be substituted with one or more halogen atom such as a chlorine atom, bromine atom or fluorine atom, hydroxy group, nitro group, methoxy, ethoxy or other such alkoxy group, carboxyl group, carbomethoxy, carboethoxy group or other such carboalkoxy group, cyano group, trifluoromethyl group, methylthio or other such alkylthio group, or phenylthio group.

Examples of the $C_6$ to $C_{12}$ aryl groups are phenyl, naphthyl, biphenyl and the like, and also aryl groups mono-substituted with a chlorine atom, bromine atom, fluorine atom, hydroxyl group, nitro group, methoxy group, ethoxy group, carboxyl group, carboethoxy group, carbomethoxy group, cyano group, trifluoromethyl group, methylthio group, phenythio group or the like, such as 2-chlorophenyl, 3-chlorophenyl, 4-chlorophenyl, 2-bromophenyl, 3-bromophenyl, 4-bromophenyl, 2-hydroxyphenyl, 3-hydroxyphenyl, 4-hydroxyphenyl, 2-nitrophenyl, 3-nitrophenyl, 4-nitrophenyl, 2-methoxyphenyl, 3-methoxyphenyl, 4-methoxyphenyl, 2-cyanophenyl, 3-cyanophenyl, 4-cyanophenyl, 2-carbomethoxyphenyl, 3-carbomethoxyphenyl, 4-carbomethoxyphenyl and the like; or disubstituted with the aforesaid groups, such as 2,3-dichlorophenyl, 2,4-dichlorophenyl, 3,4-dichlorophenyl, 2,3-dihydroxyphenyl, 2,4-dihydroxyphenyl, 3,4-dihydroxyphenyl, 2,3-dimethoxyphenyl, 2,4-dimethoxyphenyl, 3,4-dimethoxyphenyl, 2-chloro-3-bromophenyl, 2-chloro-3-hydroxyphenyl, 2-chloro-3-cyanophenyl, 2-chloro-3-methoxyphenyl, 2-hydroxy-3-chlorophenyl, 2-methoxy-3-chlorophenyl and the like; or trisubstituted with the aforesaid groups, such as 2,3,4-trichlorophenyl, 2,3,4-tribromophenyl, 2,3,4-trifluorophenyl, 2-chloro-3-hydroxy-4-methoxyphenyl, 2-hydroxy-3-hydroxy-4-methoxyphenyl and the like.

Examples of the $C_6$ to $C_{12}$ aryl groups with a $C_1$ to $C_{19}$ alkyl group are alkyl groups containing an aryl group, such as 2-methylphenyl, 3-methylphenyl, 4-methylphenyl, 2-ethylphenyl, 3-ethylphenyl, 4-ethylphenyl, 2-butylphenyl, 2-pentylphenyl, 2-hexylphenyl, 2-heptylphenyl, 2-octylphenyl, 2-nonylphenyl, 2-decylphenyl, 2-dodecylphenyl, 2-tetradecylphenyl, 2-pentadecylphenyl, 2-hexadecylphenyl, 2-heptadecylphenyl, 15-methylhexadecylphenyl, 2-eicosylphenyl, tetracosylphenyl, 3-pentylphenyl, 3-hexylphenyl, 3-heptylphenyl, 3-octylphenyl, 3 -nonylphenyl, 3-decylphenyl, 3-dodecylphenyl, 3-tetradecylphenyl, 3-pentadecylphenyl, 3-hexadecylphenyl, 3-heptadecylphenyl, 3-methylhexadecylphenyl, 3-eicosylphenyl, 3-tetracosylphenyl, 4-pentylphenyl, 4-hexylphenyl, 4-heptylphenyl, 4-octylphenyl, 4-nonylphenyl, 4-decylphenyl, 4-dodecylphenyl, 4-tetradecylphenyl, 4-pentadecylphenyl, 4-hexadecylphenyl, 4-heptadecylphenyl, 15-methylhexadecylphenyl, 4-eicosylphenyl, 4-tetracosylphenyl and the like, or these groups mono-substituted with a chlorine atom, bromine atom, fluorine atom, hydroxyl group, nitro group, methoxy group, ethoxy group, carboxyl group, carboethoxy group, carbomethoxy group, cyano group, trifluoromethyl group, methylthio group, phenythio group or the like, such as 2-methyl-3-chloro-phenyl, 2-methyl-4-chloro-phenyl, 2-methyl-5-chloro-phenyl, 3-methyl-2-chloro-phenyl, 3-methyl-4-chloro-phenyl, 3-methyl-5-chloro-phenyl, 4-methyl-2-chloro-phenyl, 4-methyl-2-chloro-phenyl, 4-methyl-3-chloro-phenyl, 4-methyl-5-chloro-phenyl, 2-methyl-3-bromo-phenyl, 2-methyl-4-bromo-phenyl, 2-methyl-5-bromo-phenyl, 3-methyl-2-bromo-phenyl, 3-methyl-4-bromo-phenyl, 3-methyl-5-bromo-phenyl, 4-methyl-2-bromo-phenyl, 4-methyl-2-bromo-phenyl, 4-methyl-3-bromo-phenyl, 4-methyl-5-bromo-phenyl, 2-methyl-3-methoxy-phenyl, 2-methyl-4-methoxy-phenyl, 2-methyl-5-methoxy-phenyl, 3-methyl-2-methoxy-phenyl, 3-methyl-4-methoxy-phenyl, 3-methyl5-methoxy-phenyl, 4-methyl-2-methoxy-phenyl, 4-methyl-3-methoxy-phenyl, 4-methyl-5-methoxy-phenyl, 2-ethyl-3-chloro-phenyl, 2-ethyl-4-chloro-phenyl, 2-ethyl-5-chloro-phenyl, 3-ethyl-2-chloro-phenyl, 3-ethyl-4-chloro-phenyl, 3-ethyl-5-chloro-phenyl, 4-ethyl-2-chloro-phenyl, 4-ethyl-2-chloro-phenyl, 4-ethyl-3-chloro-phenyl, 4-ethyl-5-chloro-phenyl, 2-ethyl-3-bromo-phenyl, 2-ethyl-4-bromo-phenyl, 2-ethyl-5-bromo-phenyl, 3-ethyl-2-bromo-phenyl, 3-ethyl-4-bromo-phenyl, 3-ethyl-5-bromo-phenyl, 4-ethyl-2-bromo-phenyl, 4-ethyl-2-bromo-phenyl, 4-ethyl-3-bromo-phenyl, 4-ethyl-5-bromo-phenyl, 2-ethyl-3-methoxy-phenyl, 2-ethyl-4-methoxy-phenyl, 2-ethyl-5-methoxy-phenyl, 3-ethyl-2-methoxy-phenyl, 3-ethyl-4-methoxy-phenyl, 3-ethyl-5-methoxy-phenyl, 4-ethyl-2-methoxy-phenyl, 4-ethyl-3-methoxy-phenyl, 4-ethyl-5 -methoxy-phenyl and the like; or disubstituted with the aforesaid groups, such as 2-methyl-3-chloro-4-chloro-phenyl, 2-methyl-3-bromo-4-chloro-phenyl, 2-methyl-3-methoxy-5-chloro-phenyl, 3-methyl-2-chloro-4-hydroxy-phenyl and the like.

Examples of the $C_1$ to $C_{19}$ alkyl groups with a $C_6$ to $C_{12}$ aryl group are arylalkyl groups with an aryl group, such as benzyl, phenethyl, phenylpropyl, phenylbutyl, phenylpentyl, phenylhexyl, phenylheptyl, phenyloctyl, phenylnonyl, phenyldecyl, phenyldodecyl, phenyltetradecyl, phenylpentadecyl, phenylhexadecyl, phenylheptadecyl, phenyloctadecyl, phenyleicosyl, phenyltetracosyl and the like, or these groups substituted with a chlorine atom, bromine atom, fluorine atom, hydroxyl group, nitro group, methoxy group, ethoxy group, carboxyl group, carboethoxy group, carbomethoxy group, cyano group, trifluoromethyl group, methylthio group, phenythio group or the like, such as 2-phenyl-3-chloro-ethyl, 2-phenyl-4-chloro-ethyl, 2-phenyl-5-chloro-ethyl, 2-phenyl-3-bromo-ethyl, 2-phenyl-4-bromo-ethyl, 2-phenyl-5-bromo-ethyl, 2-phenyl-3-methoxy-ethyl, 2-phenyl-4-methoxy-ethyl, 3-phenyl-2-chloro-ethyl, 3-phenyl-4-chloro-ethyl, 3-phenyl-5-chloro-ethyl, 3-phenyl-2-bromo-ethyl, 3-phenyl-4-bromo-ethyl, 3-phenyl-5-bromo-ethyl, 3-phenyl-4-methoxy-ethyl, 2-phenyl-4-methoxy-ethyl and the like.

The $C_6$ to $C_{12}$ aryl groups with a $C_2$ to $C_{19}$ alkenyl group will include isomers pertaining to the double bond (E, Z isomers), and examples are 2-ethenylphenyl, 3-ethenylphenyl, 2-(1-propenyl)phenyl, 3-(1-propenyl) phenyl, 2-(3-propenyl)phenyl, 3-(3-propenyl)phenyl, 2-pentenylphenyl, 2-hexenylphenyl, 2-heptenylphenyl, 2-octynylphenyl, 2-nonenylphenyl, 2-decenylphenyl, 2-dodecenylphenyl, 2-tetradecenylphenyl, 2-pentadecenylphenyl, 2-hexadecenylphenyl, 2-heptadecynylphenyl, 2-eicosenylphenyl, 3-pentenylphenyl, 3-hexenylphenyl, 3-heptenylphenyl, 3-octenylphenyl, 3-nonenylphenyl, 3-decenylphenyl, 3-dodecenylphenyl, 3-tetradecenylphenyl, 3-pentadecenylphenyl, 3-hexadecenylphenyl, 3-heptadecynylphenyl, 3-eicosynylphenyl, 4-pentenylphenyl, 4- hexenylphenyl, 4-heptenylphenyl, 4-octenylphenyl, 4-nonenylphenyl, 4-decenylphenyl, 4-dodecenylphenyl, 4-tetradecenylphenyl, 4-pentadecenylphenyl, 4-hexadecenylphenyl, 4-heptadecynylphenyl, 4-eicosenylphenyl and the like, or these groups substituted with a chlorine atom, bromine atom, fluorine atom, hydroxyl group, nitro group, methoxy group, ethoxy group, carboxyl group, carboethoxy group, carbomethoxy group, cyano group, trifluoromethyl group, methylthio group, phenythio group, or the like, examples of which are 2-pentenyl-3-chlorophenyl, 2-hexenyl-4-bromophenyl, 2-heptenyl-3-methoxyphenyl, 2-octynyl-4-hydroxyphenyl, 2-nonenyl-5-cyanophenyl, 2-decenyl-3-chlorophenyl, 2-dodecenyl-4-bromophenyl, 2-tetradecenyl-5-methoxyphenyl, 2-pentadecenyl-3-ethoxyphenyl, 3-cyanohexadecen-2-ylphenyl, 2-heptadecynyl-3-hydroxyphenyl, 2-eicosyl-4-fluorophenyl, 3-pentenyl-4-chlorophenyl, 4-pentenyl-2-chlorophenyl, 4-hexenyl-2-methoxyphenyl, 4-heptenyl-3-hydroxylphenyl, 4-octynyl-5-ethoxyphenyl, 4-nonenyl-2-fluorophenyl, 4-decenyl-5-bromophenyl, 4-dodecenyl-2-cyanophenyl, 3-carboxytetradecen-4-ylphenyl, 4-pentadecenyl-2-methoxycarbonylphenyl, 4-hexadecenyl-5-ethoxycarbonylphenyl, 4-heptadecynyl-2-methylthiophenyl, 4-eicosynyl-3-phenylthiophenyl and the like.

The $C_6$ to $C_{12}$ aryl groups with a $C_2$ to $C_{19}$ alkenyl group will include isomers pertaining to the double bond (E, Z isomers), and examples are -alkyl groups containing an aryl group such as 2-phenylethenyl, 1-phenylethenyl, 3-phenyl-2-propenyl, 3-phenyl-1-propenyl, 2-phenylbutenyl, 2-phenylpentenyl, 2-phenylhexenyl, 2-phenylheptenyl, 2-phenyloctenyl, 2-phenylnonenyl, 2-phenyldecenyl, 3-phenylbutenyl, 3-phenylpentenyl, 3-phenylhexenyl, 3-phenylheptenyl, 3-phenyloctenyl, 3-phenylnonenyl, 3-phenyldecenyl, 4-phenylpentenyl, 4-phenylhexenyl, 4-phenylheptenyl, 4-phenyloctenyl, 4-phenylnonenyl, 4-phenyldecenyl and the like, or these groups substituted with a chlorine atom, bromine atom, fluorine atom, hydroxyl group, nitro group, methoxy group, ethoxy group, carboxyl group, carboethoxy group, carbomethoxy group, cyano group, trifluoromethyl group, methylthio group, phenythio group or the like, such as 2-phenyl-3-chloro-ethenyl, 2-phenyl-4-chloro-ethenyl, 2-phenyl-5-chloro-ethenyl, 2-phenyl-3-bromo-ethenyl, 2-phenyl-4-bromo-ethenyl, 2-phenyl-5-bromo-ethenyl, 2-phenyl-3-methoxy-ethenyl, 2-phenyl-4-methoxy-ethenyl, 3-phenyl-2-chloro-ethenyl, 3-phenyl-4-chloro-ethenyl, 3-phenyl-5-chloro-ethenyl, 3-phenyl-2-bromo-ethenyl, 3-phenyl-4-bromo-ethenyl, 3-phenyl-5-bromo-ethenyl, 3-phenyl-4-methoxy-ethenyl, 2-phenyl-4-methoxy-ethenyl, 2-chloro-3-phenylbutenyl, 2-bromo-3-phenylpentenyl, 2-methoxy-3-phenylhexenyl, 2-hydroxy-3-phenylheptenyl, 2-methylthio-3-phenyloctenyl, 2-carboxy-3-phenylnonenyl, 2-methoxycarbonyl-3-phenyldecenyl, 2-chloro-4-phenylpentenyl, 3-bromo-4-phenylhexenyl, 5-cyano-4-phenylheptenyl, 3-methylthio-4-phenyloctenyl, 2-phenylthio-4-phenylnonenyl, 3-ethoxy-4-phenyldecenyl and the like.

As examples of the $C_1$ to $C_{10}$ alkoxy groups there are methoxy, ethoxy, propoxy, butoxy, pentoxy, hexoxy, heptoxy, octoxy and the like. Examples of the $C_2$ to $C_{10}$ alkoxycarbonyl groups are methoxycarbonyl, ethoxycarbonyl, propoxycarbonyl, butoxycarbonyl, pentoxycarbonyl, hexoxycarbonyl, heptoxycarbonyl and the like.

X in general formula (I) represents O, S, $CH_2$ or NH, but O or $CH_2$ is preferred.

More preferably, in general formula (I) $R_1$ to $R_{11}$ are each independently a hydrogen atom, fluorine atom, chlorine atom, bromine atom or $C_1$ to $C_5$ alkyl group, and the $C_1$ to $C_5$ alkyl group may be straight-chain or branched, examples of which are methyl, ethyl, n-propyl, isopropyl, n-butyl, isobutyl, sec-butyl, tert-butyl, n-pentyl, isopentyl, neopentyl, tert-pentyl and the like.

As examples of the pharmacologically acceptable salts, there are base-addition salts and acid-addition salts. The base-addition salts are salts which retain the biological efficacy and characteristics of the free base, without being biologically or otherwise undesirable, and include salts obtained from inorganic bases such as the sodium, potassium, lithium, ammonium, calcium and magnesium salts. They also include of course salts obtained from organic bases. For example, they include salts obtained from substituted amines such as primary amines, secondary amines, tertiary amines, natural substituted amines, cyclic amines and basic ion-exchange resins, examples of which are isopropylamine, trimethylamine, diethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purine, piperazine, piperidine, N-ethylpiperidine, ornithine, polyamine resin and the like. Again, the acid-addition salts are salts which retain the biological efficacy and characteristics of the free acid, without being biologically or otherwise undesirable, and they include inorganic acid salts such as the hydrochloride, sulphate, nitrate, hydrobromide, hydrofluoroborate, phosphate, perchlorate and the like, and organic acid salts such as the oxalate, tartrate, lactate, acetate and the like. However, the pharmacologically acceptable salts of this invention are not restricted to these.

Amongst the compounds of the present invention, in cases where there is an asymmetric carbon in the molecule, optical isomers will be present and, moreover, in cases where there are at least two asymmetric carbons diastereomers are present. The present invention will include these optical isomers and diastereomers. Furthermore, the invention will encompass stereoisomers.

The compounds of the present invention can be produced by a combination of known methods. For example, synthesis can readily be carried out by the reaction of a compound represented by formula (V) (in formula (V), Q is for example a chlorine atom or hydroxyl group) with a compound represented by formula (IV), but the method of synthesis is not restricted to this particular method.

With regard to the synthesis of Compound (IV), the production of the lactones (the case where X is an oxygen atom) can be carried out by the methods disclosed in, for example, *J. Chem. Soc. Perkin Trans.* I, 121–129 (1987), *J. Org. Chem.*, 59, 488–490 (1994), *Bull. Chem. Soc. Japan*, 52, 3601–3605 (1979), *J. Chem. Soc. Perkin Trans.* I, 1225–1231 (1987), *Tetrahedron Lett.*, 5143–5146 (1983), and *Chem. Pharm. Bull.*, 38, 94–98 (1990), and the production of the lactams (the compounds where X is NH) can be carried out by the methods disclosed in *Chem. Pharm. Bull.*, 32 (10), 4197–4204 (1984), *Pharmazie*, 43(7), 473–474 (1988), *Monatsh. Chem.*, 123(1–2), 93–98 (1992), *J. Inorg. Biochem.*, 24(3), 167–181 (1985), *J. Am. Chem. Soc.*, 107 (18), 5219–5224 (1985), *J. Org. Chem.*, 50(8), 1344–1346 (1985) and the like.

In the case where a therapeutic agent containing an effective amount of a ketone of the present invention is clinically administered, it is administered orally or parenterally. Administration forms include tablets, sugar-coated tablets, pills, capsules, powders, lozenges, solutions, suppositories and injections, and these can be produced by compounding with medically permitted fillers. The following can be given as examples of fillers. There are medically permitted fillers such as lactose, sucrose, glucose, sorbitol, mannitol, potato starch, amylopectin, various other types of starch, cellulose derivatives (for example carboxymethyl cellulose, hydroxyethyl cellulose and the like), gelatin, magnesium stearate, polyvinyl alcohol, polyethylene glycol wax, gum Arabic, talc, titanium dioxide, olive oil, peanut oil, sesame oil and other types of vegetable oil, liquid paraffin, neutral fatty base, ethanol, propylene glycol, physiological saline, sterilized water, glycerol, colouring agents, flavourings, thickeners, stabilizers, isotonic agents, buffers and the like.

In the present invention haemopoietic agent refers to a drug which, when administered to humans or animals, encourages the production of platelets, red blood cells, white blood cells and the like within the body, and which is used to prevent or treat cytopaenia brought about by cancer chemotherapy, radiotherapy, bone marrow transplantation and drug therapy, or by immunological abnormality or anaemia such as renal anaemia, haemorrhagic anaemia, haemolytic anaemia or deficiency anaemia. Moreover, the haemopoietic agents of the present invention can also be used in the field of treating aplastic anaemia, thrombocytopaenia, and hypoleukocytosis caused by infectious disease, viral disease or nutrition disorders, or idiopathic thrombocytopaenic purpura and the like. Furthermore, it can also be used for self-stored blood and the like.

It is also possible to use the haemopoietic agents of the present invention in combination with, for example, EPO which is a red haemopoietic agent or G-CSF which is a white haemopoietic agent, in the prevention or treatment of hypocytosis brought about by cancer chemotherapy, radiotherapy, bone marrow transplantation and drug therapy, or by immunological abnormality or anaemia such as renal anaemia, haemorrhagic anaemia, haemolytic anaemia, deficiency anaemia.

The amount of the therapeutic agent of the present invention employed will differ according to the symptoms, body weight, age and method of administration but, normally, there can be administered to an adult from 0.01 mg to 2000 mg per day.

EXAMPLES

Below, the present invention will be explained in still more specific terms by providing reference examples and examples.

Example 1

Synthesis of Compound 1

4-Nitrophenylacetic acid (7.2 g, 40 mmol) and then dicyclohexylcarbodiimide (8.6 g, 42 mmol) were added at room temperature to a dichloroethane (100 ml) suspension of 4-hydroxy-6-methyl-2-pyrone (5.0 g, 40 mmol), then 4-dimethylaminopyridine (0.97 g, 8.0 mmol) added and stirring carried out for 1 hour at room temperature, and then for a further 16 hours at 50° C. After returning to room temperature, the insoluble dicyclohexylurea produced was filtered off and the reaction solution washed with dilute hydrochloric acid, after which the aqueous layer was extracted with dichloromethane. After concentrating the solution, sodium hydrogen carbonate was added to the residue obtained, to form the sodium salt, and washing carried out with ethyl acetate.

The organic layer was discarded, and the aqueous layer acidified by the addition of dilute hydrochloric acid, then extraction performed with dichloromethane. After distilling off the solvent, separation and purification were performed by column chromatography. When recrystallizion was carried out from ethanol, 4-hydroxy-6-methyl-3-(4-nitrophenylacetyl)-2-pyrone (5.03 g, 44%) was obtained as pale yellow crystals. Tetrahydrofuran (50 ml), methanol (15 ml) and concentrated hydrochloric acid (5 ml) were added to the compound obtained (1.00 g, 3.46 mmol), then Pd-C (5%, wet, 200 mg) was also added, and the atmosphere replaced with hydrogen. In 3 hours the raw material was consumed and the hydrogen was replaced by argon. The precipitate was filtered off, washed with hot methanol and the filtrate concentrated. When the solid obtained was recrystallized from methanol, there was obtained 3-(4-aminophenylacetyl)-4-hydroxy-6-methyl-2-pyrone hydrochloride (760 mg, 74%). 2-Thiopheneacetyl chloride (0.17 ml, 1.5 mmol) was added to a THF (10 ml) solution of the compound obtained (400 mg, 1.35 mmol), and then triethylamine added (0.52 ml, 4.1 mmol) and stirring carried out for 1 hour at room temperature. After returning to room temperature, dilute hydrochloric acid was added and extraction performed with dichloromethane. The organic layer was dried with anhydrous sodium sulphate, and the solvent distilled off, after which separation and purification were carried out by column chromatography. When recrystallization was performed from ethanol, Compound 1 (280 mg, 54%) was obtained as pale yellow crystals.

Below, the structural formula of Compound 1 and its physical data are shown.

Melting point 156–157° C.

Elemental analysis Compositional formula $C_{20}H_{17}NO_5S$ Calculated: C, 62.65; H, 4.47; N, 3.65; S, 8.36. Measured: C, 62.15; H, 4.56; N, 3.54; S, 8.33.

NMR (ppm) (300 MHz, $CD_3OD$) 2.31 (d, J=0.82 Hz, 3H), 3.92 (s, 2H), 4.37 (s, 2H), 6.17 (q, J=0.82 Hz, 1H), 6.99–7.05 (m, 2H), 7.25–7.52 (m, 3H), 7.52–7.55 (m, 2H)

IR $(cm^{-1})$(KBr) 3304, 1719, 1663, 1609, 1547, 1415, 1257, 996, 696

Mass (EI) 383 ($M^+$)

Example 2

Synthesis of Compound 2

4-Nitrobenzaldehyde (4.5 g, 29.7 mmol) and then a number of drops of piperidine were added to a benzene (40 ml) solution of dehydroacetic acid (5.00 g, 29.7 mmol) at room temperature, after which refluxing was performed for 6 hours while eliminating water by azeotropy. The majority of the benzene was distilled of directly, and then the distillation taken to dryness under reduced pressure. Following which, when recrystallization was performed from ethanol, 4-hydroxy-6-methyl-3-(4-nitrophenyl)acryloyl-2-pyrone (7.3 g, 82%) was obtained as orange crystals.

Tetrahydrofuran (250 ml), methanol (75 ml) and concentrated hydrochloric acid (25 ml) were added to the compound obtained (5.00 g, 16.6 mmol), then Pd-C (5%, containing 100% of water, 700 mg) added and the atmosphere replaced by hydrogen. After stirring for 17 hours, the hydrogen was replaced by argon. The precipitate was filtered off, washed with hot methanol, and the filtrate concentrated. When the solid obtained was recrystallized from ethanol, 3-(4-aminophenylpropionyl)-4-hydroxy-6-methyl-2-pyrone hydrochloride (3.66 g, 71%) was obtained. 2-Thiopheneacetyl chloride (0.35 ml, 2.8 mmol) was added to a THF (10 ml) solution of the compound obtained (800 mg, 2.58 mmol), then triethylamine (1.07 ml, 7.7 mmol) added and stirring carried out for 2 hours at room temperature and for a further 4 hours at 60° C. Next, dilute hydrochloric acid was added and extraction performed with dichloromethane. The organic layer was dried with anhydrous sodium sulphate, and the solvent distilled off, after which separation and purification were carried out by column chromatography. When recrystallization was performed from ethanol, Compound 2 (570 mg, 56%) was obtained as pale yellow crystals.

Below, the structural formula of Compound 2 and its physical data are shown.

Melting point 137–139° C.

Elemental analysis Compositional formula $C_{21}H_{19}NO_5S$ Calculated: C, 63.46; H, 4.82; N, 3.52; S, 8.07. Measured: C, 63.12; H, 4.88; N, 3.47; S, 8.21.

NMR (ppm) (300 MHz, $CD_3OD$) 2.32 (d, J=0.82 Hz, 3H), 4.32 (s, 2H), 5.95 (s, 2H), 6.19 (q, J=0.82 Hz, 1H), 6.77 (br s, 1H), 6.78 (s, 1H), 6.82 (br s, 1H)

IR $(cm^{-1})$ (KBr) 1702, 1686, 1647, 1613, 1555, 1518, 1415, 1000, 706

Mass (EI) 397 ($M^+$)

Example 3

Synthesis of Compound 3

3-Nitrophenylacetic acid (7.20 g, 39.6 mmol) and then dicyclohexylcarbodiimide (8.6 g, 42 mmol) were added to a 1,2-dichloroethane (100 ml) suspension of 4-hydroxy-6-methyl-2-pyrone (5.00 g, 39.6 mmol) at room temperature, then 4-dimethylaminopyridine (0.24 g, 2.0 mmol) added and stirring carried out for 1 hour at 60° C., after which further 4-dimethylaminopyridine (0.48 g, 4.0 mmol) was added and stirring performed for 6 hours at 60° C. While the solution was still warm, the dicyclohexylurea was filtered off, and the reaction solution washed with dilute hydrochloric acid (50 ml), after which the aqueous layer was extracted with dichloromethane. After drying with anhydrous sodium sulphate, the solvent was distilled off and separation and purification carried out column chromatography. When recrystallization was performed from ethanol, 4-hydroxy-6-methyl-3-(3-nitrophenylacetyl)-2-pyrone (6.60 g, 58%) was obtained as white crystals.

Tetrahydrofuran (250 ml), methanol (75 ml) and concentrated hydrochloric acid (25 ml) were added to the compound obtained (5.00 g, 17.3 mmol), then Pd-C (5%, containing 100% of water, 800 mg) added and the atmosphere replaced by hydrogen. The raw material was consumed in 5 hours and then the hydrogen replaced by argon. The precipitate was filtered off, washed with hot methanol, and the filtrate concentrated. When the solid obtained was recrystallized from ethanol, 3-(3-aminophenylacetyl)-4-hydroxy-6-methyl-2-pyrone hydrochloride (3.9 g, 76%) was obtained. A chloroform (15 ml) solution of the compound obtained (500 mg, 1.69 mmol) was ice-cooled and 2-thiopheneacetyl chloride (0.25 ml, 2.0 mmol) added. Next, pyridine (0.4 ml, 5.0 mmol) was added and stirring carried out for 3 hours. After returning to room temperature, stirring was carried out for a further 7 hours, then dilute hydrochloric acid added and extraction performed with dichloromethane. The organic layer was dried with anhydrous sodium sulphate, and the solvent distilled off. When recrystallization was performed from ethanol, Compound 3 (295 mg, 46%) was obtained as pale yellow crystals.

Below, the structural formula of Compound 3 and its physical data are shown.

Melting point 137–140° C.

Elemental analysis Compositional formula $C_{20}H_{17}NO_5S·0.2H2O$ Calculated: C, 62.06; H, 4.53; N, 3.62. Measured: C, 62.05; H, 4.64; N, 3.68.

NMR (ppm) (300 MHz, $CDCl_3$) 2.28 (d, J=0.82 Hz, 3H), 3.94 (s, 2H), 4.39 (s, 2H), 5.94 (q, J=0.82 Hz, 1H), 7.03–7.07 (m, 3H), 7.24–7.32 (m, 3H+1H), 7.41–7.46 (m, 1H), 16.3 (s, 1H)

IR ($cm^-$) (KBr) 3290, 1721, 1665, 1620, 1562, 1547, 1439, 996, 775, 692

Mass (EI) 383 ($M^+$)

Example 4

Synthesis of Compound 4

4-Nitrophenylacetic acid (8.1 g, 45 mmol) and then dicyclohexylcarbodiimide (9.7 g, 47 mmol) were added to a dichloroethane (150 ml) suspension of 1,3-cyclohexanedione (5.00 g, 44.6 mmol) at room temperature, after which 4-dimethylaminopyridine (0.27 g, 2.2 mmol) was added and stirring carried out for 1 hour at 60° C. and then further 4-dimethylaminopyridine (0.54 g, 4.4 mmol) added and stirring carried out for 23 hours at 85° C. The dicyclohexylurea was filtered off while the solution was still warm, then the reaction solution washed with dilute hydrochloric acid (50 ml), after which the aqueous layer was extracted with dichloromethane. After drying with anhydrous sodium sulphate, the solvent was distilled off and separation and purification performed by column chromatography. When recrystallization was performed from ethanol, 3-hydroxy-2-(4-nitrophenylacetyl)-2-cyclohexenone (8.2 g, 67%) was obtained as yellow crystals. Tetrahydrofuran (100 ml), methanol (35 ml) and concentrated hydrochloric acid (10 ml) were added to the compound obtained (2.00 g, 7.3 mmol), then Pd-C (5%, containing 100% of water, 300 mg) added and the atmosphere replaced by hydrogen. The raw material was consumed in 4 hours and then the hydrogen replaced by argon. The precipitate was filtered off, washed with hot methanol, and the filtrate concentrated. When the solid obtained was recrystallized from ethanol, 2-(4-aminophenylacetyl)-3-hydroxy-2-cyclohexenone hydrochloride (1.3 g, 64%) was obtained. A chloroform (15 ml) solution of the compound (500 mg, 1.77 mmol) obtained was ice-cooled and 2-thiopheneacetyl chloride (0.26 ml, 2.1 mmol) added. Next, pyridine (0.44 ml, 5.5 mmol) was added and stirring carried out for 3 hours. After returning to room temperature, stirring was carried out for 15 hours, then dilute hydrochloric acid added and extraction performed with dichloromethane. The organic layer was dried with anhydrous sodium sulphate, and the solvent distilled off. When recrystallization was performed from ethanol, Compound 4 (245 mg, 37%) was obtained as pale yellow crystals.

Below, the structural formula of Compound 4 and its physical data are shown.

Melting point 127–128° C.

Elemental analysis Compositional formula $C_{20}H_{19}NO_4S$ Calculated: C, 65.02; H, 5.18; N, 3.79. Measured: C, 64.45; H, 5.23; N, 3.87.

NMR (ppm) (300 MHz, $CDCl_3$) 1.97 (quint, J=6.4 Hz, 2H), 2.49 (t, J=6.4 Hz, 2H), 2.66 (t, J=6.4 Hz, 2H), 3.94 (s, 2H), 4.32 (s, 2H), 7.03–7.06 (m, 2H), 7.21 (d, J=8.5 Hz, 2H), 7.29–7.32 (m, 2H, aromH+NH), 7.38 (d, J=8.5 Hz, 2H), 17.9 (s, 1H)

IR ($cm^{-1}$) (KBr) 3314, 1669, 1562, 1531, 1412, 1336, 1301, 1255, 1191, 1164, 1021, 959, 714

Mass (EI) 369 ($M^+$)

Example 5

Synthesis of Compound 5

4-Nitrophenylacetic acid (4.5 g, 25 mmol) and then dicyclohexylcarbodiimide (5.4 g, 26 mmol) were added to a 1,2-dichloroethane (160 ml) suspension of 4-hydroxycoumarin (4.00 g, 24.6 mmol) at room temperature, after which 4-dimethylaminopyridine (0.15 g, 1.2 mmol) was added and stirring carried out for 1 hour at 60° C. and then further 4-dimethylaminopyridine (0.30 g, 2.4 mmol) added and stirring carried out for 23 hours at 85° C. The dicyclohexylurea was filtered off while the solution was still warm, then the reaction solution washed with dilute hydrochloric acid (50 ml), after which the aqueous layer was extracted with dichloromethane. After drying with anhydrous sodium sulphate, the solvent was distilled off and separation and purification performed by column chromatography. When recrystallization was performed from ethyl acetate, 4-hydroxy-3-(4-nitrophenylacetyl)-coumarin (1.56 g, 19%) was obtained as yellow crystals. Tetrahydrofuran (50 ml), methanol (18 ml) and concentrated hydrochloric acid (5 ml) were added to the compound (1.00 g, 3.1 mmol) obtained, then Pd-C (5%, containing 100% of water, 150 mg) added and the atmosphere replaced by hydrogen. The raw material was consumed in 4 hours and then the hydrogen replaced by argon.

The precipitate was filtered off, washed with hot methanol, and the filtrate concentrated. When the solid obtained was recrystallized from ethanol, 3-(4-aminophenylacetyl)-4-hydroxycoumarin hydrochloride (0.85 g, 83%) was obtained. A chloroform (15 ml) solution of the compound obtained (400 mg, 1.21 mmol) was ice-cooled and 2-thiopheneacetyl chloride (0.18 ml, 1.4 mmol) added. Next, pyridine (0.30 ml, 3.6 mmol) was added and stirring carried out for 3 hours.

After returning to room temperature, stirring was carried out for 15 hours, then dilute hydrochloric acid added and extraction performed with dichloromethane. The organic layer was dried with anhydrous sodium sulphate, and the solvent distilled off. When recrystallization was performed from ethanol, Compound 5 (167 mg, 33%) was obtained as pale yellow crystals.

Below, the structural formula of Compound 5 and its physical data are shown.

Melting point 228–230° C.

High resolution mass spectrum Compositional formula $C_{23}H_{17}NO_5S$ Calculated: 419.0828. Measured: 419.0816.

NMR (ppm) (300 MHz, $CDCl_3$) 3.94 (s, 3H), 4.50 (s, 2H), 7.03–7.06 (m, 2H), 7.24–7.43 (m, 8H, arom+NH), 7.67–7.71 (m, 1H), 8.03–8.07 (m, 1H), 17.4 (s, 1H)

IR ($cm^{-1}$) (KBr) 3292, 1719, 1661, 1609, 1551, 1433, 1415, 1236, 992, 766

Mass (EI) 419 ($M^+$)

Example 6

Synthesis of Compound 6

4-Nitrophenylacetic acid (6.7 g, 37 mmol) and then dicyclohexylcarbodiimide (8.0 g, 39 mmol) were added, at room temperature, to a dichloromethane (100 ml) suspension of 6-methyl-dihydro-2,4-pyrandione (4.73 g, 36.9 mmol) which was synthesized by the hydrogenation of 4-hydroxy-6-methyl-2-pyrone, after which 4-dimethylaminopyridine (0.23 g, 1.9 mmol) was added and stirring carried out for 1 hour and then further 4-dimethylaminopyridine (0.46 g, 3.8 mmol) added and stirring carried out for 23 hours at room temperature. The dicyclohexylurea was filtered off while the solution was still warm, then the reaction solution washed with dilute hydrochloric acid (50 ml), after which the aqueous layer was extracted with dichloromethane. After drying with anhydrous sodium sulphate, the solvent was distilled off and separation and purification performed by column chromatography. When recrystallization was performed from ethanol, 4-hydroxy-6-methyl-3-(4-nitrophenylacetyl)-5,6-dihydro-2-pyrone (5.9 g, 55%) was obtained as yellow crystals. Tetrahydrofuran (100 ml), methanol (35 ml) and concentrated hydrochloric acid (10 ml) were added to the compound (2.00 g, 6.9 mmol) obtained, then Pd-C (5%, containing 100% of water, 300 mg) added and the atmosphere replaced by hydrogen. The raw material was consumed in 4 hours and then the hydrogen replaced by argon. The precipitate was filtered off, washed with hot methanol, and the filtrate concentrated. When the solid obtained was recrystallized from ethanol, 3-(4-aminophenylacetyl)-4-hydroxy-6-methyl-5,6-dihydro-2-pyrone hydrochloride (1.43 g, 70%) was obtained. A chloroform (15 ml) solution of the compound obtained (500 mg, 1.68 mmol) was ice-cooled and 2-thiopheneacetyl chloride (0.25 ml, 2.1 mmol) added. Next, pyridine (0.41 ml, 5.4 mmol) was added and stirring carried out for 3 hours. After returning to room temperature, stirring was carried out for 15 hours, then dilute hydrochloric acid added and extraction performed with dichloromethane. The organic layer was dried with anhydrous sodium sulphate, and the solvent distilled off. When recrystallization was performed from ethanol, Compound 6 (317 mg, 49%) was obtained as pale yellow crystals.

Below, the structural formula of Compound 6 and its physical data are shown.

Melting point 148–150° C.

Elemental analysis Compositional formula $C_{20}H_{19}NO_5S\cdot0.3H_2O$ Calculated: C, 61.46; H, 5.05; N, 3.58. Measured: C, 61.47; H, 5.03; N, 3.70.

NMR (ppm) (300 MHz, $CDCl_3$) 1.45 (d, J=6.2 Hz, 3H), 2.63–2.67 (m, 2H), 3.93 (s, 2H), 4.29 (d, J=15.0 Hz, 1H), 4.38 (d, J=15.0 Hz, 1H), 4.45–4.57 (m, 1H), 7.04–7.07 (m, 2H), 7.26 (d, J=8.5 Hz, 2H), 7.30–7.32 (m, 2H), 7.39 (d, J=8.5 Hz, 2H), 17.6 (s, 1H)

IR ($cm^{-1}$) (KBr) 3300, 1719, 1667, 1599, 1528, 1415, 1342, 1296, 1255, 963, 627

Mass (EI) 385 ($M^+$)

Example 7

Synthesis of Compound 7

A dichloromethane (20 ml) solution of 3-(4-aminophenyl)-4-hydroxy-6-methyl-2-pyrone hydrochloride (500 mg, 1.68 mmol) and furanacetic acid (215 mg, 1.71 mmol) was ice-cooled and triethylamine (0.49 ml, 3.5 mmol) added. Then, dicyclohexylcarbodiimide (365 mg, 1.77 mmol) was added and stirring carried out for 30 minutes. After returning to room temperature and stirring for 15 hours, dilute hydrochloric acid was added and extraction performed with dichloromethane. The organic layer was dried with anhydrous sodium sulphate and the solvent distilled off, after which separation and purification were performed by column chromatography. When recrystallization was performed from ethanol, Compound 7 (150 mg, 24%) was obtained as white crystals.

Below, the structural formula of Compound 7 and its physical data are shown.

Melting point 175–178° C.

High resolution mass spectrum Compositional formula $C_{20}H_{17}NO_6$ Calculated: 367.1056. Measured: 367.1056.

NMR (ppm) (300 MHz, $CDCl_3$) 2.67 (s, 3H), 3.77 (s, 2H), 4.37 (s, 2H), 5.94 (s, 1H), 6.31–6.42 (m, 2H), 7.24 (d, J=8.5 Hz, 2H), 7.32 (br s, 1H, NH), 7.42 (d, J=8.5 Hz, 2H), 7.44 (br s, 1H)

IR ($cm^{-1}$) (KBr) 3294, 1738, 1663, 1657, 1560, 1535, 1417, 1305, 1253, 998, 919, 727

Mass (EI) 367 ($M^+$)

Example 8

Synthesis of Compound 8

A dichloromethane (20 ml) solution of 3-(3-aminophenyl)-4-hydroxy-6-methyl-2-pyrone hydrochloride (600 mg, 2.03 mmol) and furanacetic acid (280 mg, 2.2 mmol) was ice-cooled and triethylamine (0.60 ml, 4.2 mmol) added. Then, dicyclohexylcarbodiimide (460 mg, 2.2 mmol) was added and stirring carried out for 30 minutes. After returning to room temperature and stirring for 15 hours, dilute hydrochloric acid was added and extraction performed with dichloromethane. The organic layer was dried with anhydrous sodium sulphate and the solvent distilled off, after which separation and purification were performed by column chromatography. When recrystallization was performed from ethanol, Compound 8 (156 mg, 22%) was obtained as white crystals.

Below, the structural formula of Compound 8 and its physical data are shown.

Melting point 151–152° C.

High resolution mass spectrum Compositional formula $C_{20}H_{17}NO_6$ Calculated: 367.1056. Measured: 367.1056.

NMR (ppm) (300 MHz, CDCl$_3$) 2.28 (d, J=0.82 Hz, 3H), 3.77 (s, 2H), 4.39 (s, 2H), 5.95 (q, J=0.82 Hz, 1H), 6.32–6.42 (m, 2H), 7.02–7.06 (m, 1H), 7.25–7.34 (m, 3H), 7.45–7.48 (m, 2H), 16.3 (s, 1H)

IR (cm$^-$) (KBr) 3262, 1721, 1651, 1562, 1545, 1444, 1011, 996, 841, 795, 741

Mass (EI) 367 (M$^+$)

Example 9

Dicyclohexylcarbodiimide (980 mg, 4.7 mmol) and then triethylamine (0.60 ml, 4.2 mmol) were added to a dichloromethane (20 ml) solution of tetronic acid (450 mg, 4.50 mmol) and 4-(2-thiophen-2-ylacetylamino)phenylacetic acid (900 mg, 4.51 mmol) which had been synthesized from thiopheneacetyl chloride and 4-aminophenylacetic acid, and after stirring for 30 minutes 4-dimethylaminopyridine (82 mg, 0.67 mmol) was added and stirring carried out for a further 24 hours. The dicyclohexylurea was filtered off and the reaction solution washed with dilute hydrochloric acid, after which the aqueous layer was extracted with dichloromethane. After drying with anhydrous sodium sulphate, the solvent was distilled off and separation and purification performed by column chromatography. When recrystallization was carried out from ethanol, Compound 9 (660 mg, 41%) was obtained as white crystals.

Below, the structural formula of Compound 9 and its physical data are shown.

Melting point 170–173° C.

Elemental analysis Compositional formula $C_{18}H_{15}NO_5S \cdot 0.1H_2O$ Calculated: C, 60.19; H, 4.27; N, 3.90. Measured: C, 60.04; H, 4.22; N, 3.93.

NMR (ppm) (300 MHz, CDCl$_3$) 3.94 (s, 2H), 4.15 (s, 2H), 4.58–4.68 (br d, 2H), 7.04–7.07 (m, 2H), 7.29–7.32 (m, 2H, arom+NH), 7.31 (d, J=8.5 Hz, 2H), 7.41 (d, J=8.5 Hz, 2H)

IR (cm$^-$) (KBr) 3288, 1752, 1661, 1603, 1537, 1415, 1257, 1042, 963

Mass (EI) 357 (M$^+$)

Example 10

A dichloromethane (20 ml) solution of 3-(4-aminophenyl)-4-hydroxy-6-methyl-2-pyrone hydrochloride (700 mg, 2.37 mmol) and 3-methylthiopheneacetic acid (390 mg, 2.4 mmol), which had been synthesized from 3-methylthiophene-2-aldehyde, was ice-cooled and triethylamine (0.7 ml, 4.8 mmol) added. Then, dicyclohexylcarbodiimide (515 mg, 2.5 mmol) was added, plus a small amount of dimethylaminopyridine, and stirring carried out for 20 hours at room temperature. Dilute hydrochloric acid was then added and extraction performed with dichloromethane. The organic layer was dried with anhydrous sodium sulphate and the solvent distilled off. The residue was separated and purified by column chromatography and when recrystallization was performed from ethanol, Compound 10 (352 mg, 37%) was obtained as white crystals.

Below, the structural formula of Compound 10 and its physical data are shown.

Melting point 137–138° C.

Elemental analysis Compositional formula $C_{21}H_{19}NO_5S \cdot 0.5H_2O$ Calculated: C, 62.05; H, 4.96; N, 3.45. Measured: C, 62.17; H, 4.69; N, 3.52.

NMR (ppm) (300 MHz, CDCl$_3$) 2.27 (s, 3H), 2.32 (d, J=0.82 Hz, 3H), 3.85 (s, 2H), 4.38 (s, 2H), 6.18 (q, J=0.82 Hz, 1H), 6.88 (d, J=5.2 Hz, 1H), 7.20 (d, J=5.2 Hz, 1H), 7.27 (d, J=8.5 Hz, 2H), 7.53 (d, J=8.5 Hz, 2H)

IR (cm$^-$) (KBr) 3296, 1742, 1721, 1644, 1609, 1562, 1533, 1415, 1238, 1183, 998

Mass (EI) 397 (M$^+$)

Example 11

Haemopoietic action in ordinary mice

Using Compound 1 as the test drug, this was administered intravenously over a consecutive four day period to C57BL/6 mice (6 weeks old, male) (n=6) at a dose of 10 mg/kg, and 7 days following the commencement of the administration the number of blood cells in the peripheral blood was measured.

Figure 1:
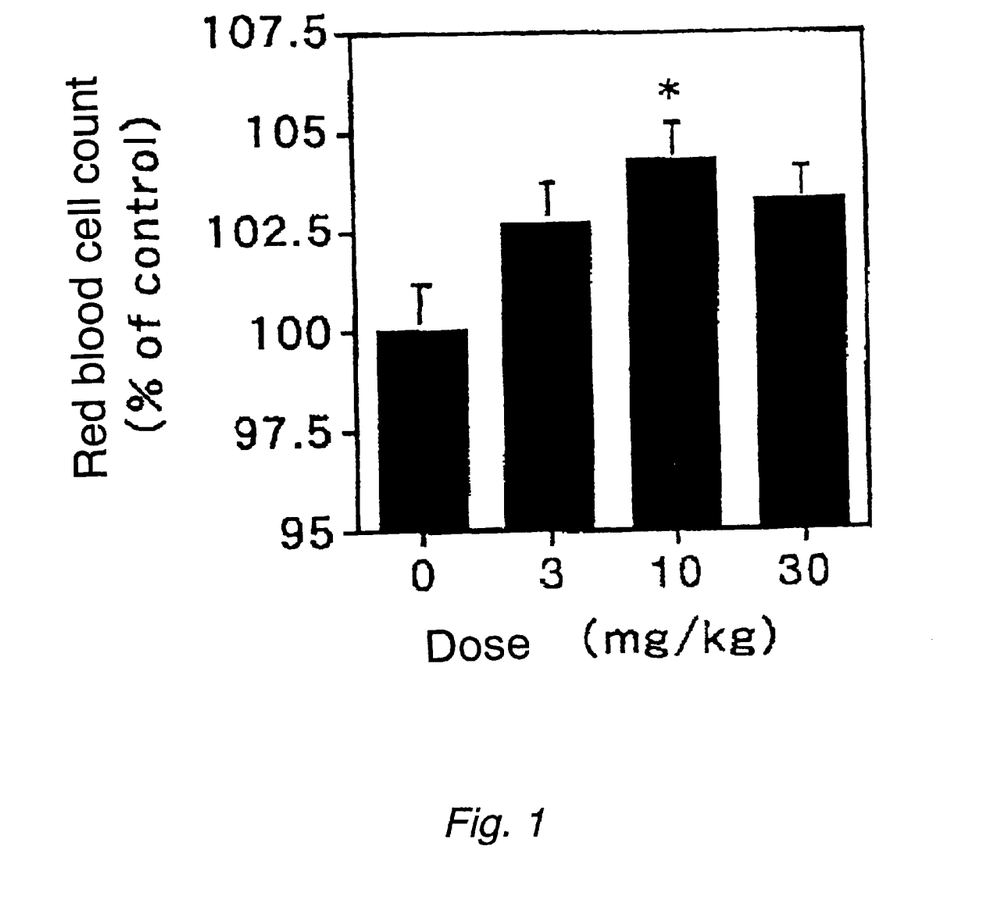
FIG. 1 is a graph showing the haemopoietic action in Example 11.

FIG. 1 shows the percentage increase in terms of a control group (taken as 100%).

From the results, it is clear that the test drug significantly increases the red blood cells, demonstrating the value in medical applications of the compounds described in this patent.

Industrial Utilization Potential

The ketones of the present invention bring about a significant increase in red blood cells and other cells, and are effective as outstanding haemopoietic agents in medicine, in particular for the prevention or treatment of cytopaenia brought about by cancer chemotherapy, radiotherapy, bone marrow transplantation or drug therapy, or by immunological abnormality or anaemia.

What is claimed is:

1. A ketone derivative represented by the following general formula (I)

where A is general formula (II) or (III)

m is the integer 1 or 2, $R_1$ to $R_7$ are each independently a hydrogen atom or a substituent selected from the group consisting of a fluorine atom, chlorine atom, bromine atom, $C_2$ to $C_{19}$ alkyl groups, $C_1$ to $C_{19}$ alkenyl groups, $C_6$ to $C_{12}$ aryl groups, $C_6$ to $C_{12}$ aryl groups with a $C_1$ to $C_{19}$ alkyl group, $C_1$ to $C_{19}$ alkyl groups with a $C_6$ to $C_{12}$ aryl group, $C_6$ to $C_{12}$ aryl groups with a $C_2$ to $C_{19}$ alkenyl group, $C_2$ to $C_{19}$ alkenyl groups with a $C_6$ to $C_{12}$ aryl group, the hydroxyl group, $C_1$ to $C_{10}$ alkoxy groups, the nitro group, carboxyl group, $C_2$ to $C_{10}$ alkoxycarbonyl groups, and the cyano group, or $R_1$ and $R_2$ are together —CH=CH—CH=CH—, $R_5$ and $R_6$ are together —CH=CH—CH=CH— or —$(CH_2)_q$— where q is an integer in the range 2 to 5, or $R_6$ and $R_7$ are together —$(CH_2)_r$— where r is an integer in the range 2 to 5, $R_8$ and $R_9$ are each independently a hydrogen atom, or a substitutent selected from the group consisting $C_2$ to $C_6$ alkyl groups, $C_1$ to $C_6$ alkenyl groups, $C_6$ to $C_{12}$ aryl groups, $C_6$ to $C_{12}$ aryl groups with a $C_1$ to $C_{19}$ alkyl group, $C_1$ to $C_{19}$ alkyl groups with a $C_6$ to $C_{12}$ aryl group, $C_6$ to $C_{12}$ aryl groups with a $C_2$ to $C_{19}$ alkenyl group, $C_2$ to $C_{19}$ alkenyl groups with a $C_6$ to $C_{12}$ aryl group, $C_2$ to $C_{10}$ alkoxycarbonyl groups, or $R_8$ and $R_9$ are together —$(CH_2)_4$— or —$(CH_2)_5$—, $R_{10}$ is a fluorine atom, chlorine atom or bromine atom, $R_{11}$ is a $C_1$ to $C_6$ alkyl group or $C_6$ to $C_{12}$ aryl group, or $R_{10}$ and $R_{11}$ are together —CH=CH—CH=CH— or —$(CH_2)_t$— where t is an integer in the range 2 to 5, X is O or S, Z is a hydrogen atom or methyl group, Y is O or S, n is 0 or 1, or a pharmacologically acceptable salt thereof.

2. A ketone derivative according to claim 1, or a pharmacologically acceptable salt thereof, where $R_1$ to $R_{11}$ are each independently a hydrogen atom, fluorine atom, chlorine atom, bromine atom, $C_1$ to $C_5$ alkyl group, or phenyl group.

3. A ketone derivative according to claim 1, or a pharmacologically acceptable salt thereof, where A is represented by general formula (II).

4. A ketone derivative according to claim 1, or a pharmacologically acceptable salt thereof, where A is represented by general formula (III).

5. A ketone derivative according to claim 1, or a pharmacologically acceptable salt thereof, where Z is a hydrogen atom.

6. A ketone derivatives according to claim 1, or a pharmacologically acceptable salt thereof, where X is O or $CH_2$.

7. A pharmacological composition comprising a ketone derivative of claim 1, or pharmacologically acceptable salts thereof.

8. A haemopoietic composition in which a ketone derivative according to claim 1, or pharmacologically acceptable salt thereof, is an active component.

9. A method of preventing or treating cytopaenia comprising administering to a person in need of same an effective amount of a compound of claim 1.

* * * * *